United States Patent [19]

Porter

[11] Patent Number: 5,064,435

[45] Date of Patent: Nov. 12, 1991

[54] SELF-EXPANDING PROSTHESIS HAVING STABLE AXIAL LENGTH

[75] Inventor: Christopher H. Porter, Woodenville, Wash.

[73] Assignee: Schneider (USA) Inc., Minneapolis, Minn.

[21] Appl. No.: 544,923

[22] Filed: Jun. 28, 1990

[51] Int. Cl.$^5$ .............................................. A61F 2/04
[52] U.S. Cl. ..................................... 623/12; 606/151; 606/198
[58] Field of Search ....................... 623/1, 11, 12, 13; 604/96, 104; 606/151, 153, 155, 158, 191, 198

[56] References Cited

U.S. PATENT DOCUMENTS

| | | |
|---|---|---|
| 3,868,956 | 3/1975 | Alfidi et al. |
| 4,553,545 | 11/1985 | Maass et al. ........................ 604/104 |
| 4,572,186 | 2/1986 | Gould et al. ........................ 604/104 |
| 4,649,922 | 3/1987 | Wiktor .................................. 623/1 |
| 4,655,771 | 4/1987 | Wallsten .............................. 623/1 |
| 4,681,110 | 7/1987 | Wiktor . |
| 4,699,611 | 10/1987 | Bowden ............................. 604/105 |
| 4,732,152 | 3/1988 | Wallsten et al. .................... 623/1 |
| 4,733,665 | 3/1988 | Palmaz ................................ 623/1 |
| 4,793,348 | 12/1988 | Palmaz . |
| 4,800,882 | 1/1989 | Gianturco ............................ 623/13 |
| 4,830,003 | 5/1989 | Wolff et al. .......................... 623/1 |
| 4,848,343 | 7/1989 | Wallsten et al. .................... 604/271 |
| 4,856,516 | 8/1989 | Hillstead ............................. 623/1 |
| 4,886,062 | 12/1989 | Wiktor ................................. 623/1 |

OTHER PUBLICATIONS

*Interventional Radiology*, "Self-Expanding Metallic Stents for Small Vessels: An Experimental Evaluation", Duprat et al, pp. 469–472, vol. 162, Feb. 1987.

"Self-Expanding Endovascular Prosthesis: An Experimental Study", *Radiology*, 1987 (Sep.), pp. 709–714, Rousseau et al.

"When Hope is All In Vein", *Sweden Now*, Mar., 1988.

"Transluminally-Placed Coilspring Endarterial Tube Grafts", Charles T. Dotter, MD, pp. 239–332, *Investigative Radiology*, Sep.-Oct. 1969, vol. 4.

*Technical Developments and Instrumentation*, "Transluminal Expandable Nitinol Coil Stent Grafting: Preliminary Report", Dotter et al, pp. 259–260, Radiology 147, Apr. 1983.

"Atherosclerotic Rabbit Aortas: Expandable Intraluminal Grafting", *Radiology*, 1986 (Sep.), pp. 723–726, Palmaz et al.

*Primary Examiner*—Randy Citrin Shay
*Attorney, Agent, or Firm*—Haugen and Nikolai

[57] ABSTRACT

A body implantable stent consists of two or more generally tubular, coaxial and slidably connected stent segments. Each of the stent segments is of open weave construction, formed of multiple braided, helically wound strands of resilient material. The stent is elastically deformed to a reduced radius when deployed. When released after positioning, the stent self-expands radially into contact with a tissue wall segment defining a blood vessel or other body cavity. As each stent segment expands radially, it contracts in the axial direction. To preserve a consistent length of the stent in spite of axial contraction of the segments, the axially outward and non-overlapping portions of the stent can be designed for secure fixation to the tissue wall segment, for example as radially outward flares. Accordingly, axial contraction occurs as a reduction in the length of the medial regions where adjacent stent segments overlap. Alternative approaches to maintain axial length include the addition of reinforcing filaments near the stent opposite ends to increase the restoring force, the provision of fixation hooks at opposite ends of the stent, and securing an elongate, axially directed, flexible and inextensible wire to the opposite ends of the stent.

26 Claims, 2 Drawing Sheets

SELF-EXPANDING PROSTHESIS HAVING STABLE AXIAL LENGTH

BACKGROUND OF THE INVENTION

The present invention relates to body implantable devices, and more particularly to prostheses and grafts intended for long-term or permanent fixation in body cavities.

A wide variety of patient treatment and diagnostic procedures involve the use of devices inserted into the body of the patient, with some of these devices being permanently implanted. Among these devices are prostheses or grafts for transluminal implantation, for example as disclosed in U.S. Pat. No. 4,655,771 (Wallsten). The prosthesis described in Wallsten is a flexible tubular braided structure formed of helically wound thread elements. Gripping members at opposite ends of the prosthesis initially secure it to a catheter, with the proximal gripping member being movable distally to give the prosthesis the shape of a balloon. In deployment, the gripping members and catheter are removed, leaving the prosthesis to assume a substantially cylindrical shape as it slightly expands and substantially conforms to a blood vessel wall or other tissue. Another prosthesis is disclosed in U.S. Pat. No. 4,681,110 (Wiktor). A flexible tubular liner, constructed of braided strands of a flexible plastic, is insertable into the aorta, whereupon it self-expands against an aneurysm to direct blood flow past the aneurysm. The braided stents of Wallsten and Wiktor axially contract as they radially expand.

Another elastic stent is shown in U.S. Pat. No. 4,830,003 (Wolff et al). The stent includes a series of generally longitudinal wires welded together in pairs, with the wires in each pair then bent into a "V" shape. Like the braided stents, this stent shortens axially as it radially expands.

Prostheses also have been constructed of plastically deformable materials. U.S. Pat. No. 4,733,665 (Palmaz) discloses intraluminal vascular grafts radially expanded using angioplasty balloons. The grafts are wire mesh tubes, and axially shorten as they radially expand. U.S. Pat. No. 4,800,882 (Gianturco) features a stent formed of wire, including a plurality of serpentine bends to form opposed loops. A balloon is inflated to radially expand the stent, without substantial axial shortening.

Yet another approach to prosthesis design is shown in U.S. Pat. No. 3,868,956 (Alfidi et al). Alfidi et al discloses a strainer or screen with a plurality of generally longitudinal wires, bound together by a cylindrical sleeve. The wires are deformable into a longitudinal, straight-line configuration for implantation. Once implanted, the device is heated. Due to the recovery property of the metal forming the wires (e.g. nitinol alloy), heating causes the wires to flare radially outward at the opposite ends, thus to secure the device at the desired location.

A stent including means for maintaining a constant axial length in spite of radial expansion or contraction, is disclosed in U.S. Pat. No. 4,553,545 (Maass et al), as a prosthesis in the form of a helical coil spring. In one embodiment, a constant axial length of the spring is maintained, with opposite ends of the spring rotated relative to one another to change the spring pitch and radius. An alternative approach involves maintaining a constant pitch over a given section of a spring, by providing spring material to a "constant length" section from a more compressed section of the spring. In each case, the spring preferably is elastic, with a memory favoring the radially expanded configuration.

A self-expanding stent or prosthesis often is preferred over a plastically deformed device. Resilient stents can be deployed without dilatation balloons or other stent expanding means. A self-expanding stent can be preselected in accordance with the diameter of the blood vessel or other fixation site. While deployment requires skill in positioning the prosthesis, the added skill of properly dilating the balloon to plastically expand a prosthesis to a selected diameter is not required. Also, the self-expanding device remains at least slightly compressed after fixation, and thus has a restoring force which facilitates acute fixation. By contrast, the plastically expanded stent must rely on the restoring force of deformed tissue, or on hooks, barbs or other independent fixation means.

Further advantages arise from constructing the prosthesis of multiple, braided and helically wound strands or filaments as in the aforementioned Wallsten patent. The filaments themselves have a restoring force which causes the filaments to bear against tissue walls of the body cavity in which the stent is fixed, thus maintaining the cavity open. At the same time there is sufficient space between adjacent filaments to promote embedding of the stent into the tissue, and fibrotic growth to enhance long-term fixation. A further advantage of this construction is that it enables a substantial radial contraction of the prosthesis during deployment, for example to as little as about one-fourth of the normal diameter (the diameter in the relaxed state, i.e. when subject to no external forces). This facilitates deployment of the prosthesis through narrow vessels or other constrictions on the way to the point of fixation.

At the same time, a substantial axial elongation accompanies the radial contraction. There is a substantial axial contraction or shortening as the stent self expands, once free of its radial constraint. Thus, there is a rubbing or scraping action axially along tissue as the radially expanding stent also axially shortens. Should tissue at the fixation area further yield to radial prosthesis expansion in the longer term, such expansion causes further axial shortening and wiping action, and presents further risk of injury to tissue. A further drawback is that a stent during its fixation may radially expand more than expected, retaining less than the intended or minimum necessary axial length. Likewise, a plastically deformable stent may require more than the anticipated radial expansion and axial shortening.

Therefore, it is an object of the present invention to provide a prosthesis of open weave, helical and braided construction capable of substantially maintaining its axial length as it radially self-expands.

Another object is to provide a radially expanding tubular stent comprised of at least two stent segments, with an area of overlap of the sections variable in axial length to maintain a consistent axial separation between non-overlapping ends of the stent.

Yet another object is to provide a stent with a medial portion variable in axial length, in combination with means at the opposite end portions of the stent for fixing the stent to bodily tissue, such that the bodily tissue maintains a substantially constant axial separation of the two end portions during any radial expansion or contraction of the stent.

SUMMARY OF THE INVENTION

To achieve these and other objects, there is provided a body implantable device, including coaxial first and second open weave stent segments slidably engaged to form a stent. The stent segments are engaged along respective concentric first and second axially inward portions overlapping one another to form a medial region of the stent. Further, the stent segments include opposite non-overlapping first and second axially outward regions with respective and opposite first and second ends of the stent. The stent segments, at least along the axially inward portions, have a predetermined first diameter and a predetermined first axial length. The stent segments are radially compressible to a second diameter less than the first diameter and to a second axial length longer than the first axial length, to facilitate an axial insertion of the stent into a body cavity for delivery to a selected location along the body cavity and subsequent fixation of the stent to a cavity wall segment defining the body cavity. During its fixation, the stent radially expands. The first and second axially inward portions slide relative to one another to reduce the axial length of the medial region during the radial expansion. Thus the stent maintains a substantially constant axial length during radial expansion.

A preferred approach uses means for fixing the outward ends of a self-expanding stent, e.g. respective first and second flared outer end portions along the axially outward regions of the stent. The first and second ends have diameters greater than the first diameter when the stent is in the relaxed state, and when compressed tend to have a greater restoring force against the cavity wall segment, as compared to the remainder of the stent. The end diameters should be greater than the medial region diameter by five percent or more, ensuring a substantial difference in restoring force for a relatively constant diameter of the cavity along the tissue wall segment.

Alternatively, the outer end portion of each stent segment can have the same diameter as the medial region, but be composed of larger diameter filaments, added windings of filaments or otherwise have increased stiffness or resistance to radial contraction as compared to the medial region Yet another alternative is to provide fixation elements, for example hooks, at the opposite ends of the stent.

In combination with positive fixation of the stent ends, a substantial medial overlapping region is provided when the stent segments are in a radially compressed or delivery configuration. For example, the overlapping region may comprise three-fourths or more of the axial length of the compressed stent. Then, upon deployment of the stent, both stent segments radially expand and axially shorten. With the outer ends of the stent fixed, the axial shortening occurs only along the medial region, substantially shortening the region of overlap but maintaining the desired axial separation of the opposite stent ends.

An open weave of braided, helically wound strands or filaments is the preferred structure of the tubular stent. The open weave structure enables substantial self-expansion in the stent, for example to a fixation diameter at least three times the diameter during delivery. This of course results in a substantial corresponding axial shortening in each of the stent segments, but due to the overlapping medial region of the stent, the overall axial length remains virtually constant.

A pliable catheter is a suitable apparatus for delivery and deployment of the stent. More particularly, a pliable sheath can surround at least the distal end portion of the catheter and extend beyond the distal tip to surround the stent segments as well, maintaining them in a radially compressed delivery configuration. The catheter can be provided with a lumen, through which a guide wire may be inserted to facilitate travel of the catheter and compressed stent through blood vessels or other body cavities to the fixation area. Once the catheter is inserted properly to position the stent at the desired fixation point, the outer sheath is withdrawn proximally, with the stent abutting the catheter and thus secured against proximal travel with the sheath. The distal portion of the stent self-expands first, and in expanding against tissue, secures the stent segment against proximal travel. With one end of the stent constrained by tissue and the opposite end constrained by a stationary catheter, the axial length of the stent remains substantially constant. Axial shortening of the stent segments, which accompanies their radial expansion, tends to diminish the length of the medial region and leave the overall axial length unaffected.

Following fixation, further yielding of the tissue segment can result in further radial expansion of the stent. However, with the opposite ends of the stent secure, any axial shortening of the stent segments again affects only the medial overlapping region. Thus, the advantages of the open weave construction are retained, without an undesirable shortening of the stent as it radially self-expands.

IN THE DRAWINGS

For a further understanding of the above and other features and advantages, reference is made to the following detailed description and the drawings, in which:

FIG. 12 is a side elevation of another alternative device, in a radially expanded condition;

FIG. 13 is a side elevation of a further alternative device, in a radially expanded condition;

FIG. 14 is a side elevation of another alternative device, in a radially expanded condition; and FIG. 15 is a side elevation of yet another alternative device, in a radially expanded condition.

DETAILED DESCRIPTION OF THE PREFERRED EMBODIMENT

Figure 1:
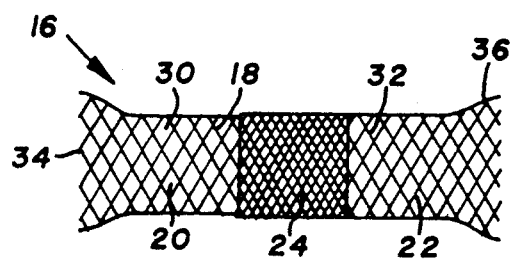
FIG. 1 is a side elevation of a body implantable device constructed in accordance with the present invention.

Turning now to the drawings, there is shown in FIG. 1 a body implantable prosthesis or stent 16. Stent 16 has an open mesh or weave construction, formed of helically wound and braided strands or filaments 18 of a resilient material, for example a body compatible stainless steel or an elastomer, e.g. polypropylene, polyurethane, polysulfone or a polyester.

Stent 16 includes coaxial proximal and distal stent segments 20 and 22. A medial region 24 is formed by the overlapping of respective axially inward portions of stent segments 20 and 22. Axially outward, non-overlapping portions of the stent segments are indicated at 30 and 32, respectively. At opposite ends of the stent are flared ends 34 and 36, each having a greater radius than the nominal radius over the majority of the stent length. As is later explained, flared ends 34 and 36 provide a fixation feature useful to maintain a constant overall axial length in stent 16, even while stent segments 20 and 22 radially self-expand and axially contract during fixation.

In FIG. 1, stent 16 is shown in its relaxed condition, with no external forces applied to radially contract the stent. Stent 16 is self-expanding in the sense that when not subject to external forces, it assumes a diameter much larger than the diameter illustrated in FIGS. 2 and 3. In these figures, the stent is elastically deformed and maintained in a radially reduced configuration by a pliable, dielectric sheath 38 surrounding the stent.

Figure 2:
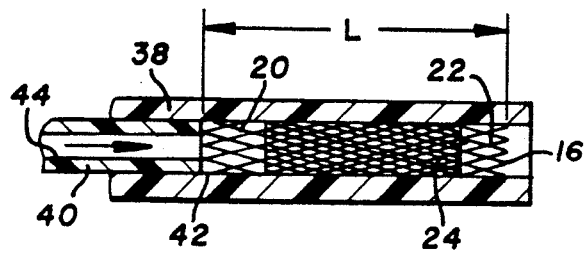
FIG. 2 is a side sectional view of a catheter and sheath retaining the implantable device in a radially compressed condition.

An elongate and pliable catheter 40, of which just the distal end region is shown in FIG. 2, includes a distal tip 42 which abuts the proximal end of the stent. The proximal portion of sheath 38 surrounds the distal end region of the catheter. Catheter 40 has a central lumen 44 open to tip 42 and running the length of the catheter, to permit delivery of a drug, in liquid form, to the catheter distal tip from a supply at the proximal end of the catheter. Lumen 44 further enables the use of a guide wire (not shown) which can be intravenously inserted, by its distal end to the desired point of fixation for stent 16. With the guide wire in place, catheter 40, stent 16 and sheath 38 are positioned to surround the proximal end of the guide wire with the guide wire contained within lumen 44. Then, the catheter, sheath and stent are moved distally or advanced, directed by the guide wire to the fixation location, whereupon the guide wire can be withdrawn.

Sheath 38 preferably is constructed of silicone rubber or other suitable biocompatible material, and surrounds the stent and catheter at least along the catheter distal end region, or along the full length of the catheter if desired. Sheath 38 preferably is thin to facilitate intravascular insertion of the catheter, sheath and stent, yet is sufficiently thick to maintain stent 16 in a reduced radius or delivery configuration against the restoring force of strands 18. The outside diameter of the assembly including the catheter, stent and sheath is approximately 2.3 millimeters.

Stent 16 is particularly well suited for use as a prosthesis or graft in a blood vessel or other body cavity. One advantageous use of the stent occurs in connection with percutaneous transluminal coronary angioplasty (PTCA) procedures. While such procedures afford significantly reduced cost and risk as compared to coronary bypass operations, acute closure and recurrence of stenosis are significant problems in up to about thirty percent of constricted or blocked passages opened by balloon angioplasty. The fixation of stent 16 within a blood vessel along a previously occluded region tends to keep this region permanently open.

Figure 3:
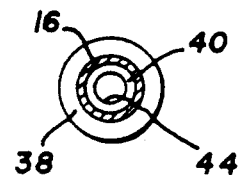
FIG. 3 is an end view of the device, catheter and sheath.

Fixation of stent 16, within a blood vessel 46 having a tissue wall segment 48, begins with intravascular insertion of the stent, catheter and sheath in the delivery configuration shown in FIGS. 2 and 3. The reduced radius facilitates insertion of this assembly through blood vessel 46 until stent 16 reaches a predetermined fixation location along the blood vessel. Once the proper positioning of the stent is confirmed, e.g. through use of one or more radiopaque markings on the stent, sheath or catheter, sheath 38 is moved proximally with respect to catheter 40.

With distal tip 42 abutting stent 16, the catheter prevents the stent from traveling proximally with sheath 38 as the sheath is withdrawn. Thus, as seen from FIG. 4, stent 16 becomes free of sheath 38 over an increasing distal portion of its axial length. As each of stent segments 20 and 22 becomes free, it radially self-expands until contacting tissue wall segment 48, then undergoes slightly further radial expansion until the tendency to radially expand is counterbalanced by the restoring force exerted radially inward by the tissue wall segment. At the equilibrium condition, shown in FIG. 5, stent is not fully radially expanded to the relaxed configuration shown in FIG. 1, and thus applies a restoring force which tends to maintain the stent at the fixation position within vessel 46.

A salient feature of the present invention is the concentric and slidable mounting of stent segments 20 and 22 in combination with the fixation provided by flared ends 34 and 36. During initial withdrawal of sheath 38, the distal flared end 36 is the first to encounter tissue wall segment 48. Due to its larger nominal (relaxed state) diameter, flared end 36 tends to radially expand somewhat more than the remainder of axially outward portion 32 of this segment, and applies comparatively greater restoring force in the radially outward direction against the tissue wall segment. Accordingly, the axial shortening of distal stent segment 22 which accompanies radial expansion, e.g. from a length of 100 mm when delivered to a fixation length of 50 mm, occurs almost entirely by travel of axially inward portion 28, distally or rightwardly as viewed in FIG. 4. The slidable engagement of segments 20 and 22 permits such distal travel while proximal segment 20 remains substantially fixed relative to catheter 40.

Figure 4:
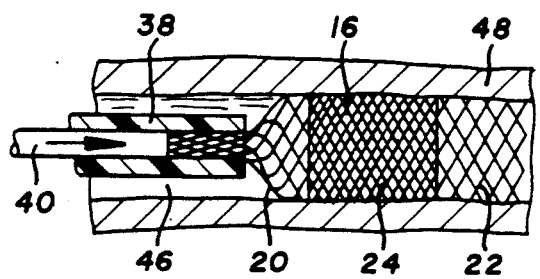
FIG. 4 is a side sectional view showing deployment of the device within a body cavity.

As sheath 38 is further withdrawn, proximal segment 20 likewise radially expands and axially shortens As illustrated in FIG. 4, much of axially outward portion 30 of segment 20 remains radially compressed within sheath 38, and thus is held fixed with respect to the catheter. Consequently, the axial contraction of proximal stent segment 20 during radial expansion occurs almost entirely by virtue of proximal travel of its axially inward portion. This of course involves further sliding of the stent segments relative to one another, and further reduces the axial length of medial overlapping region 24.

Figure 5:
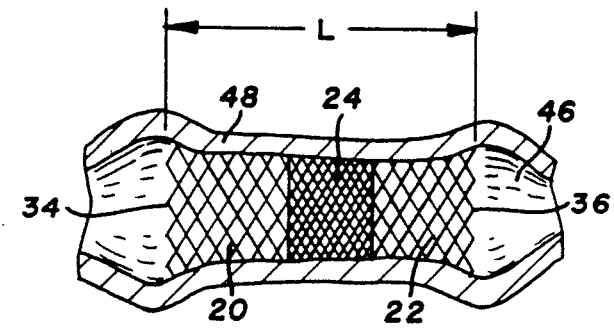
FIG. 5 is a side view of the device fixated within the cavity.

As seen from FIGS. 2 and 5, the total axial length of stent 16, designated "L", is substantially the same whether the stent is in the deployment state, or the radially expanded to equilibrium or fixation. Proximal stent segment 20 and distal stent segment 22 are each substantially shorter in equilibrium. However, virtually all of the reduction in axial length is reflected in the substantially reduced length of medial overlapping region 24, which accounts for more than three-fourths of the total stent length in FIG. 2, and only about one-fifth of the overall stent length in FIG. 5.

Eventually, fixation of stent 16 becomes permanent by virtue of the embedding of strands 18 into tissue wall segment 48, and fibrotic growth of tissue between and around strands to anchor the stent. This type of fixation occurs over a period of weeks, and in the intervening time, tissue wall segment 48 may yield to allow further radial expansion of a stent, and further axial shortening of stent segments 20 and 22. The axial length "L" remains substantially constant nonetheless, as this further axial contraction is again reflected in a further shortening of the medial overlapping region. Axial contraction occurs along the medial region, since flared ends 34 and 36 continue to exert a comparatively greater restoring force against the tissue, thus more securely anchoring the ends as compared to the central portions of the stent. Thus, the overall length of the stent is maintained not only during and immediately after fixation, but in the interim until fibrosis permanently secures the stent.

Figure 6:
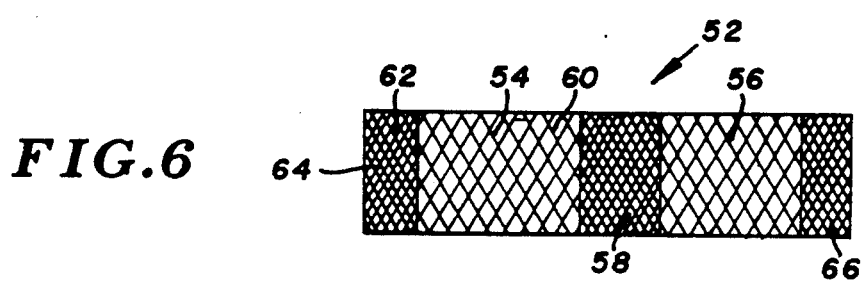
FIG. 6 is a side elevation of an alternative embodiment device in the relaxed or fully radially expanded condition.

FIG. 6 shows an alternative embodiment stent 52, again with concentric and slidably connected proximal and distal stent segments as indicated at 54 and 56. Axially inward portions of the stent segments overlap to form a medial region 58. Stent 52 has an open mesh or weave construction, formed of helically wound and braided filaments 60.

Stent 52, illustrated in its relaxed or unstressed state, does not include radially outward flares at its opposite ends. In lieu of flared ends, each of stent segments 54 and 56 includes at its axially outward end a plurality of reinforcing strands 62 connected to the braided filaments 60, thus to create respective proximal and distal reinforced end regions 64 and 66. The reinforcing strands 62 can, but need not, be of the same construction as the base filaments. In either event, the reinforcement strands lend further elastic resistance to radial compression, such that a given elastic radial compression of stent 52 requires a greater force at reinforced end regions 64 and 66 as compared to the force required between these regions.

Stent 52 can be deployed in the manner described above in connection with stent 16. Following proper positioning of the stent within a blood vessel or other body cavity, a surrounding sheath similar to sheath 38 is withdrawn proximally from its surrounding relation with stent 52, allowing the stent to radially self-expand into contact with the tissue forming the cavity. Again, stent 52 is selected to have a nominal diameter (in the relaxed state) greater than the diameter of the body cavity, so that base filaments 60 and reinforcement strands 62 engage the tissue before full expansion, and are contained short of full expansion by body tissue, for an equilibrium of the restoring force in the stent and the oppositely directed restoring force in the body tissue. With the stent in equilibrium (as shown in FIG. 5 in connection with stent 16), reinforced end regions 64 and 66 may or may not flare slightly radially outward from the remainder of the stent. In either event, the restoring force at the reinforced end regions is greater than the restoring force along the remainder of the stent length. Accordingly, the opposite ends of stent 52 tend to remain secure in their axial positioning relative to the body tissue, with axial contraction occurring as substantial reduction in the length of medial region 58.

Figure 7:
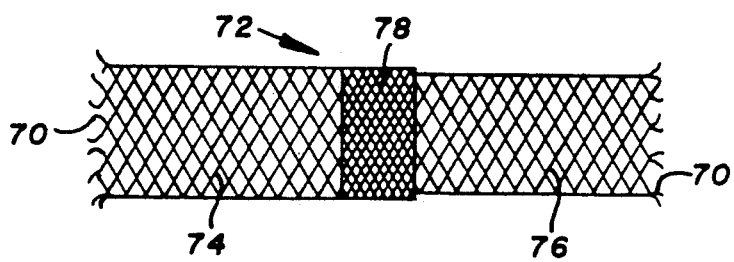
FIG. 7 is a side elevation showing yet another alternative device in the expanded or relaxed condition.

FIG. 7 illustrates yet another approach to preserving the axial length of the stent, in this case, a plurality of fixation hooks 70 at the opposite ends of a stent 72 having a slidably interconnected and coaxial proximal and distal stent segments 74 and 76. Fixation hooks 70 present some risk of injury and thus are more limited in their application than the fixation alternatives previously discussed. Nonetheless, hooks 70 provide a positive and immediate fixation of stent 72 within a cavity at the opposite stent ends. Subsequent radial expansion and axial contraction of stent segments 74 and 76 serves to reduce the length of a medial region 78, preserving the overall length of the stent.

Figure 8:
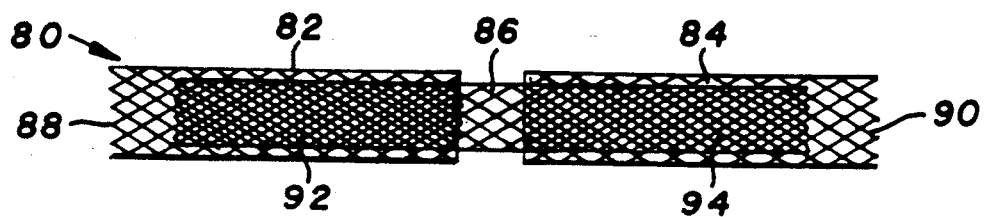
FIG. 8 is a side elevation illustrating a further alternative device in a radially compressed state.
Figure 9:
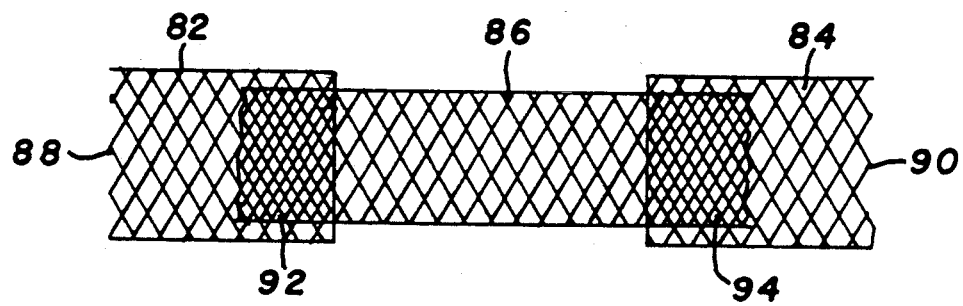
FIG. 9 is a side elevation of the device of FIG. 8 in the expanded condition.

FIGS. 8 and 9 illustrate a further embodiment stent or prosthesis 80 including a proximal segment 82, a distal segment 84 and a center segment 86 slidably engaged with the proximal and distal segments. All three segments of prosthesis 80 have the previously described open mesh or weave construction of braided filaments. Stent 80 thus includes two overlapping regions intermediate its proximal and distal ends 88 and 90, namely a proximal intermediate region 92 and a distal intermediate region 94. While center segment 86 is shown with a smaller radius than the other segments for convenience of illustration, all segments preferably have substantially the same radius.

FIG. 9 illustrates stent 80 in the relaxed or radially expanded state. Each of segments 82, 84 and 86 has a reduced axial dimension as well as a larger radius. Nonetheless, the axial distance between proximal end 88 and distal end 90 remains about the same, with virtually all of the axial contraction reflected in the substantially reduced axial dimensions of intermediate overlapping regions 92 and 94.

Prosthesis 80 can be deployed in the manner described above in connection with other embodiments. Following the desired positioning of the prosthesis within a blood vessel or other body cavity, a surrounding sheath is withdrawn slidably or folded back from a surrounding relation to the prosthesis, permitting it to radially self-expand into contact with a tissue wall segment forming the cavity (not shown). Of course, the diameter of the cavity should be less than the normal or radially expanded diameter of the prosthesis. Prosthesis 80 does not utilize any special end fixation structure such as the earlier described hooks, reinforced ends or flared ends. Rather, the prosthesis is positioned by virtue of the self-expansion and restoring force of the segments, to maintain their relative positions, particularly during their deployment and release from a sheath or the like, but also after fixation. It should be noted that this approach is suitable for the two-segment stents earlier described, although some type of end fixation means facilitates maintaining a constant axial length of the stent. If desired, a fixation structure can be provided at ends 88 and 90.

Figure 10:
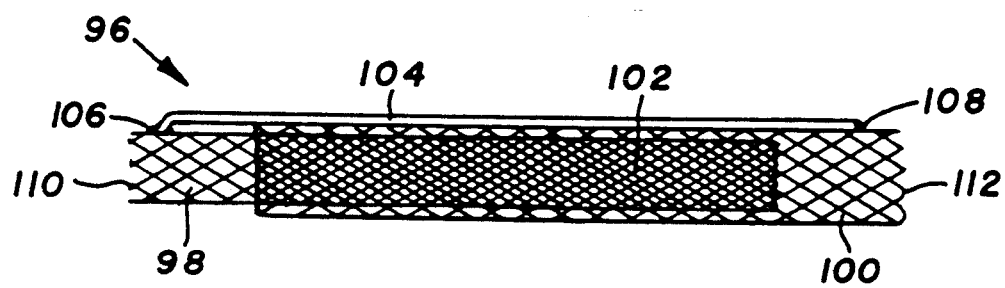
FIG. 10 is a side elevation showing yet another alternative device, in a radially compressed condition.
Figure 11:
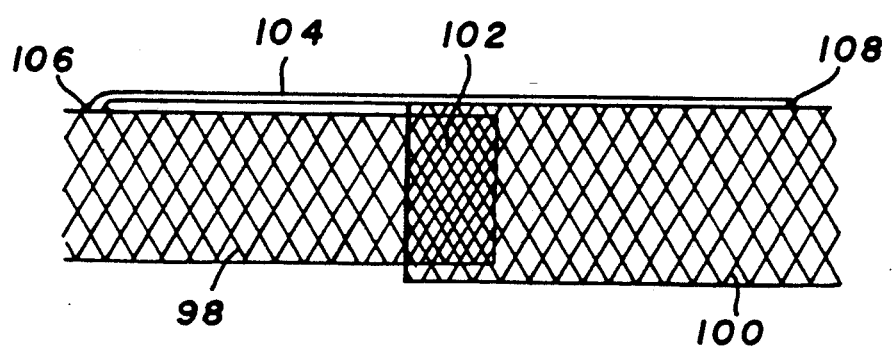
FIG. 11 is a side elevation of the device of FIG. 10 in the radially expanded condition.

FIGS. 10 and 11 illustrate yet another embodiment stent 96 including proximal and distal segments 98 and 100, slidably engaged and overlapping along a medial region 102. A strand or wire 104 runs parallel to stent 96 and is secured at points 106 and 108 near proximal and distal ends 110 and 112, respectively. Wire 104 is sufficiently flexible to bend along with stent segments 98 and 100 during delivery of the stent to the point of fixation. Yet the wire is stiff and substantially inextensible in the axial direction. Consequently wire 104 maintains a constant axial separation of proximal end 110 and distal end 112, whether stent segments 98 and 100 are radially confined as shown in FIG. 10 or radially expanded as seen in FIG. 11. With wire 104 positively determining the total length of stent 96, all of the axial contraction of stent segments 98 and 100 is reflected in the reduction of medial overlapping region 102. While the provision and securement of one or more wires 104 add to the cost of stent 96 as compared to other embodiments, the wire ensures that the stent length remains constant, regardless of the amount of radial expansion during fixation.

FIG. 12 shows a stent 114 having a proximal segment 116, a distal segment 118 and a center segment 120. The proximal and distal segments overlap the center segment along regions 121 and 122, respectively. Opposite flared ends 124 and 126 have radii greater than the nominal radius over the majority of the stent length, and thus provide a fixation feature similar to that of stent 16.

FIG. 13 illustrates a stent 128 including a proximal segment 130, a distal segment 132 and a center segment 134, with overlapping regions 136 and 138. As indicated at 140 and 142, reinforcing strands are provided at opposite ends of stent 128 to increase the elastic resistance to radial compression, in the same manner as described in connection with stent 52.

FIG. 14 shows a stent 144 having a proximal end segment 146, a distal end segment 148 and a central segment 150. Overlap occurs along intermediate regions 152 and 154. A plurality of hooks 156 enhance fixation of the opposite ends of the stent.

FIG. 15 features another alternative stent 158 having a proximal end segment 160, a distal end segment 162 and a center segment 164, with overlapping regions at 166 and 168. A strand or wire 170 runs parallel to the stent and is secured to the proximal and distal ends of the stent at points 172 and 174, respectively. Wire 170 is stiff and substantially inextensible in the axial direction, to maintain a constant axial separation of the proximal and distal ends regardless of whether the stent is radially expanded or radially confined.

The above embodiments all feature an open weave or braided construction of resilient filaments for a self-expanding stent or prosthesis. As an alternative, the stents can be constructed of plastically deformable strands. Such stents are delivered in a reduced-radius configuration, and after positioning, are radially expanded by dilating a catheter balloon or the like, e.g. as in the aforementioned Palmaz patent. Moreover, which the disclosed embodiments are employed in blood vessels, it is to be appreciated that these stent designs are suited for other body cavities as well, e.g. the urethra, biliary tree or tracheobronchial tree. Regardless of whether hooks, reinforcing strands or outwardly flared end portions are employed for outer end fixation, the full axial length of the stent is maintained substantially constant, unaffected by radial expansion and accompanying axial contraction of the engaged stent segments. Accordingly, upon deployment and in the ensuing weeks after fixation, the functional advantages of a helically wound, braided filament design are achieved without the disadvantages associated with axial shortening.

What is claimed is:

1. A device for fixation in a body cavity, comprising: a stent including generally tubular and coaxial first and second open weave stent segments slidably engaged along respective first and second axially inward portions overlapping one another to form a medial region of the stent, said stent segments further including respective non-overlapping first and second axially outward regions including respective and opposite first and second ends of the stent; said stent segments, at least along said axially inward portions, having a predetermined first diameter and a predetermined first axial length, said stent segments being radially compressible to a second diameter less than said first diameter and to a second axial length longer than said first axial length, to facilitate an axial insertion of said stent into a body cavity for delivery to a selected location therealong and subsequent fixation of the stent within the cavity by effecting an engagement of the stent segments with a tissue wall segment defining said body cavity; and wherein said first and second axially inward portions slide relative to one another to reduce the axial length of said medial region as said stent segments radially expand into said engagement, thus to maintain a substantially constant axial length of said stent during said radial expansion.

2. The device of claim 1 wherein:
each of said stent segments is an open weave construction of helically wound filaments of a resilient, body-compatible material.

3. The device of claim 2 wherein:
said material is a plastic.

4. The device of claim 2 wherein:
said material is stainless steel.

5. The device of claim 1 further including:
an elongate, flexible and substantially inextensible member running axially and connected to said first and second stent segments proximate said first and second ends, for maintaining the axial length of the stent constant during said radial expansion.

6. The device of claim 2 further including:
a means for fixing said first and second ends to said tissue wall segment.

7. The device of claim 6 wherein:
said fixing means comprises first and second pluralities of fixation hooks mounted to the stent at said first and second ends, respectively.

8. The device of claim 6 wherein:
said stent segments are flexible and have said predetermined first diameter and first axial length when not subject to external force, and are elastically compressible to said second diameter.

9. The device of claim 8 wherein:
said fixing means comprises elastic reinforcing strands connected to said filaments along first and second outer end portions including said first and second ends, respectively.

10. The device of claim 8 wherein:
said fixing means comprises first and second flared outer end portions of said first and second axially outward regions, respectively, whereby said first and second ends have diameters greater than said first diameter when the stent is in the relaxed state.

11. The device of claim 10 wherein:
the diameters of said first and second ends are greater than said first diameter by at least five percent.

12. The device of claim 11 wherein:
the axial length of each of said flared outer end portions is less than one-third of the axial length of its associated one of said stent segments.

13. A device for fixation in a body cavity, comprising:

a stent including a plurality of generally tubular and coaxial open weave stent segments, serially arranged, with adjacent stent segments slidably engaged and overlapping one another to form a plurality of intermediate overlapping regions between proximal and distal ends of said stent;

said stent segments having a predetermined first diameter and a predetermined first axial length, said stent segments further being radially compressible to a second diameter less than the first diameter and to a second axial length longer than the first axial length, to facilitate an axial insertion of said stent into a body cavity for delivery to a selected location therealong and subsequent fixation of the stent within the cavity by effecting an engagement of the stent segments with a tissue wall segment defining said body cavity; and wherein said stent segments slide relative to one another along said intermediate overlapping regions to reduce the axial length of said intermediate regions as the stent segments radially expand into said engagement, thus to maintain a substantially constant axial length of the stent during said radial expansion.

14. The device of claim 13 further including:

an elongate, flexible and substantially inextensible member running axially and connected to said stent proximate said proximal and distal ends, for maintaining the axial length of the stent constant during said radial expansion.

15. The device of claim 13 wherein:

said stent segments are elastically radially compressible from said predetermined first diameter to said second diameter.

16. The device of claim 15 wherein:

each of said stent segments is constructed of helically wound filaments of a resilient, body-compatible material.

17. The device of claim 16 wherein:
said material is a plastic.

18. The device of claim 16 wherein:
said material is stainless steel.

19. The device of claim 16 further including:
a means for fixing said proximal and distal ends to said tissue wall segment.

20. The device of claim 19 wherein:
said fixing means comprises elastic reinforcing strands connected to said filaments along first and second outer end portions including said proximal and distal ends, respectively.

21. The device of claim 19 wherein:
said fixing means comprises first and second pluralities of fixation hooks mounted to the stent at said proximal and distal ends, respectively.

22. The device of claim 19 wherein:
said fixing means comprises first and second flared end portions proximate and including said proximal and distal ends, whereby the proximal and distal ends have diameters greater than said first diameter when the stent is in the relaxed state.

23. The device of claim 22 wherein:
the diameters of said proximal and distal ends are greater than the first diameter by at least five percent.

24. The device of claim 23 wherein:
the axial length of each of said flared end portions is less than one-third of the axial length of its associated one of said stent segments.

25. A process for fixing a prosthesis within a body cavity, comprising the steps of:

slidably interconnecting a plurality of open weave stent segments to form a stent having at least one intermediate region of overlapping adjacent stent segments between proximal and distal ends of said stent;

radially compressing the stent segments into a predetermined first diameter and first axial length, axially inserting the stent into a body cavity, and delivering the stent to a selected location along the body cavity; and with said stent at said selected location, radially expanding and axially contracting the stent segments until the stent segments engage a tissue wall segment defining the body cavity to fix the stent within the body cavity, while maintaining the distance between said proximal and distal ends substantially constant.

26. The process of claim 25 wherein:

said stent segments are resilient, and said step of radially compressing the stent segments includes elastically compressing said segments into said first diameter and maintaining them in the first diameter with a restraining means, and wherein said step of radially expanding the stent segments includes removing the restraining means whereby the stent segments radially self-expand.

* * * * *